United States Patent
Coulton et al.

(10) Patent No.: US 7,468,367 B2
(45) Date of Patent: Dec. 23, 2008

(54) ETHYLENE DIAMINE DERIVATIVES AND THEIR USE AS OREXIN-RECEPTOR ANTAGONISTS

(75) Inventors: Steven Coulton, Harlow (GB); Amanda Johns, Harlow (GB); Roderick Alan Porter, Harlow (GB)

(73) Assignee: Smithkline Beecham p.l.c., Brentford, Middlesex (GB)

( * ) Notice: Subject to any disclaimer, the term of this patent is extended or adjusted under 35 U.S.C. 154(b) by 306 days.

(21) Appl. No.: 10/498,884

(22) PCT Filed: Dec. 13, 2002

(86) PCT No.: PCT/GB02/05665

§ 371 (c)(1), (2), (4) Date: Jun. 16, 2004

(87) PCT Pub. No.: WO03/051872

PCT Pub. Date: Jun. 26, 2003

(65) Prior Publication Data

US 2005/0159421 A1    Jul. 21, 2005

(30) Foreign Application Priority Data

Dec. 19, 2001 (GB) ................... 0130341.1

(51) Int. Cl.
| | |
|---|---|
| A01N 43/58 | (2006.01) |
| A01N 43/60 | (2006.01) |
| A01N 43/54 | (2006.01) |
| A01N 43/78 | (2006.01) |
| A01N 43/76 | (2006.01) |
| A01N 43/56 | (2006.01) |
| A61K 31/50 | (2006.01) |
| A61K 31/495 | (2006.01) |
| A61K 31/505 | (2006.01) |
| A61K 31/425 | (2006.01) |
| A61K 31/42 | (2006.01) |
| A61K 31/415 | (2006.01) |
| C07D 239/02 | (2006.01) |
| C07D 241/36 | (2006.01) |
| C07D 277/00 | (2006.01) |
| C07D 263/52 | (2006.01) |
| C07D 263/00 | (2006.01) |
| C07D 413/00 | (2006.01) |
| C07D 498/00 | (2006.01) |
| C07D 213/00 | (2006.01) |

(52) U.S. Cl. ............... 514/249; 544/297; 544/353; 548/200; 548/217; 548/374.1

(58) Field of Classification Search ........... 514/249, 514/275, 365, 376, 406; 544/297, 353; 548/200, 548/217, 374.1
See application file for complete search history.

(56) References Cited

U.S. PATENT DOCUMENTS

| | | | |
|---|---|---|---|
| 5,149,700 A | * | 9/1992 | Ellingboe et al. ............ 514/275 |
| 5,444,062 A | * | 8/1995 | Coe et al. ............... 514/266.21 |
| 6,008,230 A | | 12/1999 | Oku et al. ................... 514/311 |
| 6,159,964 A | * | 12/2000 | Ali et al. ..................... 514/221 |

FOREIGN PATENT DOCUMENTS

| | | |
|---|---|---|
| WO | WO91/18904 | 12/1991 |
| WO | WO92/07844 | 5/1992 |
| WO | WO 00/47576 | 8/2000 |
| WO | WO 00/47577 | 8/2000 |
| WO | WO 01/23357 | 4/2001 |
| WO | WO 02/098363 | 12/2002 |

OTHER PUBLICATIONS

Salin-Pascual et al, "Hypothalamic Regulation of Sleep" Neuropsychopharmacology, vol. 25, (S5), pp. S21-27 (2001).*
Smart and Jerman, "The physiology and pharmacology of the orexins" Pharmacology & Therapeutics, vol. 94, pp. 51-61 (2002).*

* cited by examiner

*Primary Examiner*—Zachary C Tucker
(74) *Attorney, Agent, or Firm*—Kathryn L. Sieburth; Mary F. McCarthy; Charles M. Kinzig

(57) ABSTRACT

This invention relates to heterocyclic substituted ethylene diamine derivatives and their use as pharmaceuticals.

15 Claims, No Drawings

SEQUENCE LISTING

<160> NUMBER OF SEQ ID NOS: 1

<210> SEQ ID NO 1
<211> LENGTH: 35
<212> TYPE: PRT
<213> ORGANISM: Homo sapien

<400> SEQUENCE: 1

Glu Pro Leu Pro Asp Cys Cys Arg Gln Lys Thr Cys Ser Cys Arg Leu
 1               5                  10                  15

Tyr Glu Leu Leu His Gly Ala Gly Asn His Ala Ala Gly Ile Leu Thr
            20                  25                  30

Leu Asn His
        35

ETHYLENE DIAMINE DERIVATIVES AND THEIR USE AS OREXIN-RECEPTOR ANTAGONISTS

This application is a 371 of International Application No. PCT/GB02/05665, filed 13 Dec. 2002.

This invention relates to heterocyclic substituted ethylene diamine derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder; depressive neurosis/disorder, anxiety neurosis; dysthymic disorder; behaviour disorder; mood disorder; sexual dysfunction; psychosexual dysfunction; sex disorder, sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; nausea, vomiting; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegenerative disorders, which includes nosological entities such as disinhibition-dementia-parkinsonism-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see Cell, 1998, 92, 573–585.

There is a significant incidence of obesity in westernised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-term complications of the disease. Insulin sensitisers will be useful for many diabetics, however they do not have an anti-obesity effect Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

The present invention provides heterocyclic substituted ethylene diamine derivatives which are non-peptide antagonists of human orexin receptors, in particular orexin-1 receptors. In particular, these compounds are of potential use in the treatment of obesity, including obesity observed in Type 2 (non-insulin-dependent) diabetes patients, and/or sleep disorders, and/or stroke, particularly ischemic or haemorrhagic stroke, and/or for blocking the emetic response i.e. useful in the treatment of nausea and vomiting.

International Patent Applications WO99/09024, WO99/58533, WO00/47577, and WO00/47580, disclose phenyl urea derivatives and WO00/47576, discloses quinolinyl cinnamide derivatives as orexin receptor antagonists.

According to the invention there is provided compounds of formula (I):

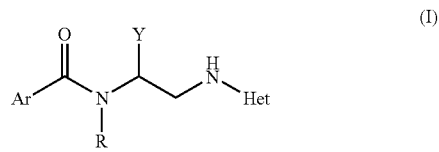

wherein:

R represents an optionally substituted $(C_{1-4})$alkyl;

Y represents hydrogen or an optionally substituted $(C_{1-4})$alkyl;

Het represents an optionally substituted 5- or 6-membered heteroaryl group containing up to 3 heteroatoms selected from N, O, and S, or an optionally substituted bicyclic heteroaryl group containing up to 3 heteroatoms selected from N, O and S;

Ar represents a phenyl or a 5- or 6-membered heteroaryl group containing up to 3 heteroatoms selected from N, O and S, wherein the phenyl or heteroaryl group is substituted by $R^3$, and further optional substituents; or Ar represents an optionally substituted bicyclic aromatic or heteroaromatic group containing up to 3 heteroatoms selected from N, O and S;

$R^3$ independently represents hydrogen, an optionally substituted ($C_{1-4}$)alkoxy, halo, optionally substituted ($C_{1-6}$)alkyl, optionally substituted phenyl, or an optionally substituted 5- or 6-membered heterocyclic ring containing up to 3 heteroatoms selected from N, O and S;

or pharmaceutically acceptable derivatives thereof, provided the compound is not N-[2-(7-chloro-quinolin-4-ylamino)ethyl]-N-methyl-phthalamic acid or N-methyl-n-[2-napthalen-2-ylaminoethyl]benzamide.

Examples of 5- or 6-membered heteroaryl group containing up to 3 heteroatoms selected from N, O and S, include furanyl, thienyl, pyrrolyl, oxazolyl, thiazolyl, imidazolyl, oxadiazolyl, thiadiazolyl, pyridyl, triazolyl, triazinyl, pyridazinyl, pyrimidinyl, isothiazolyl, isoxazolyl, pyrazinyl or pyrazolyl.

When Het represents a bicyclic heteroaryl it may be selected from isoquinolinyl, quinoxalinyl, benzoxazolyl, quinolinyl, napththyridinyl, benzofuranyl, benzimidazolyl, benzothienyl, indolyl, benzothiazoyl or quinazolinyl.

Examples of where Ar represents an optionally substituted bicyclic aromatic or heteroaromatic include naphthyl, quinolinyl, napththyridinyl, benzofuranyl, benzimidazolyl, benzoxazolyl, isoquinolinyl, quinoxalinyl or quinazolinyl.

Preferably R is optionally substituted methyl.

Preferably Het represents pyrimidinyl, benzoxazolyl or quinoxalinyl.

Preferably when Ar represents phenyl, or a 5- or 6-membered heteroaryl group the substituent $R^3$ is ortho to the amide carbonyl group.

Preferably Ar represents optionally substituted thiazolyl or pyrazolyl.

Examples of groups where $R^3$ is a 5- or 6-membered heterocyclic ring containing up to 3 heteroatoms selected from N, O and S, include furanyl, thienyl, pyrrolyl, oxazolyl, thiazolyl, imidazolyl, oxadiazolyl, thiadiazolyl, pyridyl, triazolyl, triazinyl, pyridazyl, pyrimidinyl, isothiazolyl, isoxazolyl, pyrazinyl, pyrazolyl, piperidine, piperazine, thiomorpholine or morpholine.

Preferably $R^3$ represents trifluoromethoxy, methoxy, ethoxy, halo, or optionally substituted phenyl, pyridyl, pyrazolyl, pyrimidinyl or oxadiazolyl group.

Even more preferably $R^3$ represents an optionally substituted phenyl, e.g. 4-fluorophenyl.

Optional substituents for the groups Y, R, $R^3$, Ar and Het include halogen, hydroxy, oxo, cyano, nitro, ($C_{1-4}$)alkyl, ($C_{1-4}$)alkoxy, halo($C_{1-4}$)alkyl, halo($C_{1-4}$)alkoxy, ($C_{1-4}$)acyl, aryl, aryl($C_{1-4}$)alkyl, aryl($C_{1-4}$)alkoxy, ($C_{1-4}$)alkylthio, ($C_{1-4}$)alkylamino($C_{1-4}$)alkyl, hydroxy($C_{1-4}$)alkyl, hydroxy($C_{1-4}$)alkoxy, ($C_{1-4}$)alkoxy($C_{1-4}$)alkyl, ($C_{3-6}$)cycloalkyl($C_{1-4}$)alkoxy, ($C_{1-4}$)alkanoyl, ($C_{1-4}$)alkoxycarbonyl, ($C_{1-4}$)alkylsulfonyl, ($C_{1-4}$)alkylsulfonyloxy, ($C_{1-4}$)alkylsulfonyl($C_{1-4}$)alkyl, arylsulfonyl, arylsulfonyloxy, arylsulfonyl($C_{1-4}$)alkyl, ($C_{1-4}$)alkylsulfonamido, ($C_{1-4}$)alkylamido, ($C_{1-4}$)alkylsulfonamido($C_{1-4}$)alkyl, ($C_{1-4}$)alkylamido($C_{1-4}$)alkyl, arylsulfonamido, arylcarboxamido, arylsulfonamido($C_{1-4}$) alkyl, arylcarboxamido($C_{1-4}$)alkyl, aroyl, aroyl($C_{1-4}$)alkyl, or aryl($C_{1-4}$)alkanoyl group; a group $R^aR^bN$—, $R^aR^bN(CH_2)n$-, $R^aR^bN(CH_2)nO$—, $R^aOCO(CH_2)_r$, $R^aCON(R^b)CH_2)_r$, $R^aR^bNCO(CH_2)_r$, $R^aR^bNSO_2(CH_2)_r$, or $R^aSO_2NR^b(CH_2)_r$, where each of $R^a$ and $R^b$ independently represents a hydrogen atom or a ($C_{1-4}$)alkyl group or where appropriate $R^aR^b$ forms part of a ($C_{3-6}$)azacycloalkane or ($C_{3-6}$)(2-oxo)azacycloalkane ring, n represents an integer from 1 to 4, and r represents zero or an integer from 1 to 4. Additionally when the substituent is $R^aR^bN(CH_2)n$- or $R^aR^bN(CH_2)nO$, $R^a$ with at least one $CH_2$ of the $(CH_2)n$ portion of the group form a ($C_{3-6}$)azacycloalkane and $R^b$ represents hydrogen, a ($C_{1-4}$)alkyl group or with the nitrogen to which it is attached forms a second fused ($C_{3-6}$)azacycloalkane.

Preferred optional substituents for Ar are halogen, cyano, ($C_{1-4}$)alkyl, hydroxy($C_{1-4}$)alkyl, $R^aR^bN(CH_2)n$ or $R^aR^bN$.

Preferred optional substituents for Het are halogen, cyano, ($C_{1-4}$)alkyl, hydroxy($C_{1-4}$)alkyl, ($C_{1-4}$)acyl, ($C_{1-4}$)alkoxy ($C_{1-4}$)alkyl, $R^aR^bNCO(CH_2)$, $R^aR^bN(CH_2)n$ or $R^aR^bN$.

Preferred optional substituents for $R^3$ are halogen, $R^aR^bN$ and $R^aR^bN(CH_2)nO$.

In addition Het may be optionally substituted by a phenyl ring optionally substituted by a halogen, cyano, or $C_{1-4}$alkanoyl or $C_{1-4}$alkylsulfonyl group; or by a 5- or 6-membered heterocyclic ring, optionally substituted by a ($C_{1-2}$)alkyl or $R^aR^bN$— group; wherein $R^a$ and $R^b$ are as defined above.

In the groups Ar and Het, substituents positioned ortho to one another may be linked to form a fused ring.

When a halogen atom is present in the compound of formula (I) it may be fluorine, chlorine, bromine or iodine.

When used herein the term aryl means a 5- or 6-membered ring, for example phenyl, or a 7- to 12-membered bicyclic ring system where at least one of the rings is aromatic, for example naphthyl.

When the compound of formula (I) contains an alkyl group, whether alone or forming part of a larger group, e.g. alkoxy or alkylthio, the alkyl group may be straight chain, branched or cyclic, or combinations thereof, it is preferably methyl or ethyl.

It will be appreciated that compounds of formula (I) may exist as R or S enantiomers. The present invention includes within its scope all such isomers, including mixtures. Where additional chiral centres are present in compounds of formula (I), the present invention includes within its scope all possible diastereoismers, including mixtures thereof. The different isomeric forms may be separated or resolved one from the other by conventional methods, or any given isomer may be obtained by conventional synthetic methods or by stereospecific or asymmetric syntheses.

It will be understood that the invention includes pharmaceutically acceptable derivatives of compounds of formula (I) and that these are included within the scope of the invention.

Particular compounds according to the invention include those mentioned in the examples and their pharmaceutically acceptable derivatives.

As used herein "pharmaceutically acceptable derivative" includes any pharmaceutically acceptable salt, ester or salt of such ester of a compound of formula (I) which, upon administration to the recipient is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further feature of the invention there is provided a process for the preparation of compounds of formula (I) and salts thereof. The following schemes detail synthetic routes to compounds of the invention.

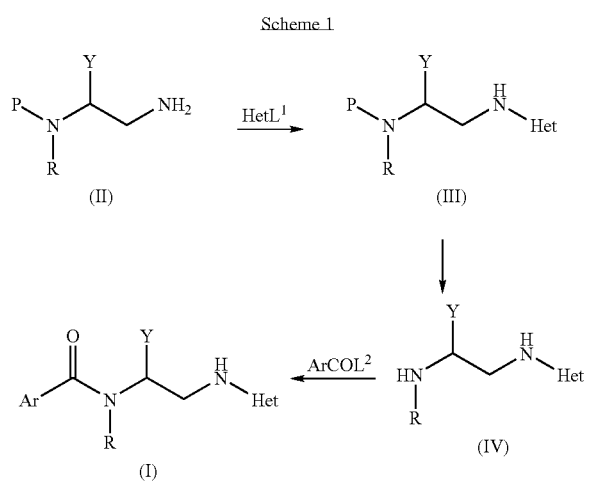

Wherein Het, Ar, R and Y are as defined for formula (I), $L^1$ and $L^2$ are leaving groups, and P is a protecting group.

Reaction of (II) with HetL$^1$ proceeds in an inert solvent such as dimethylformamide, xylene or THF at ambient or elevated temperature. A base such as potassium carbonate or N,N-diisopropylethylamine may be used.

Examples of suitable leaving groups $L^1$ include chlorine, fluorine and triflate.

Examples of protecting groups P include t-butyloxycarbonyl, trifluoroacetyl and benzyloxycarbonyl. Deprotection conditions are respectively, acid (e.g. trifluoroacetic acid in dichloromethane), base (e.g. sodium hydroxide in a solvent such as aqueous methanol) and catalytic hydrogenolysis in an inert solvent (e.g using palladium on charcoal in a lower alcohol or ethyl acetate).

Examples of suitable leaving groups $L^2$ include halogen, OC(=O)alkyl and OC(=O)O-alkyl. The transformation (IV) to (I) may be carried out in an inert solvent such as dichloromethane, in the presence of a base such as triethylamine. Alternatively this step may be carried out when $L^2$ represents hydroxy, in which case reaction with (IV) takes place in an inert solvent such as dichloromethane in the presence of a diimide reagent such as 1-ethyl-3-(3-dimethylaminopropyl)carbodiimide hydrochloride, and an activator such as 1-hydroxybenzotriazole. Also where $L^2$ represents hydroxy the reaction can be effected using O-(7-azabenzotriazol-1-yl)-N,N,N',N'-tetramethyluronium hexafluorophosphate (HATU) with a base such as triethylamine or N,N-diisopropylethylamine.

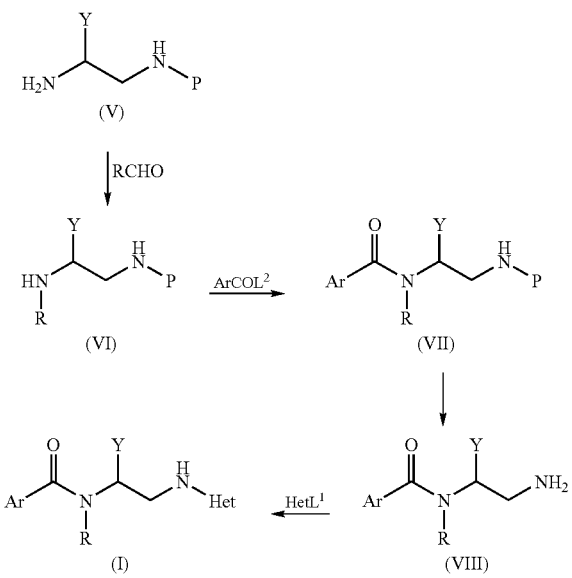

Wherein Het, Ar, R and Y are as defined for formula (I), $L^1$ and $L^2$ are leaving groups, and P is a protecting group.

A compound of formula (VI) may be prepared by reacting a compound of formula (V) with an aldehyde, R'CHO. Suitable reducing agents which may be employed include sodium borohydride, sodium cyanoborohydride or sodium triacetoxyborohydride under acidic conditions, or catalytic hydrogenation. The reaction may conveniently be effected in a solvent such as ethanol or dichloroethane.

Examples of protecting groups P include t-butyloxycarbonyl, trifluoroacetyl and benzyloxycarbonyl. Deprotection conditions are respectively, acid (e.g. trifluoroacetic acid in dichloromethane), base (e.g. sodium hydroxide in a solvent such as aqueous methanol) and catalytic hydrogenolysis in an inert solvent (e.g using palladium on charcoal in a lower alcohol or ethyl acetate).

Reaction of (VIII) with HetL$^1$ proceeds in an inert solvent such as dimethylformamide, xylene or THF at ambient or elevated temperature . A base such as potassium carbonate or N,N-diisopropylethylamine may be used.

Examples of suitable leaving groups $L^1$ include chlorine, fluorine and triflate.

Examples of suitable leaving groups $L^2$ include halogen, OC(=O)alkyl and OC(=O)O-alkyl. The transformation (III) to (I) may be carried out in an inert solvent such as dichloromethane, in the presence of a base such as triethylamine. Alternatively this step may be carried out when $L^2$ represents hydroxy, in which case reaction with (III) takes place in an inert solvent such as dichloromethane in the presence of a diimide reagent such as 1-ethyl-3-(3-dimethylaminopropyl)carbodiimide hydrochloride, and an activator such as 1-hydroxybenzotriazole. Also where $L^2$ represents hydroxy the reaction can be effected using O-(7-azabenzotriazol-1-yl)-N,N,N',N'-tetramethyluronium hexafluorophosphate (HATU) with a base such as triethylamine or N,N-diisopropylethylamine.

Compounds of formula (II) and (V) are known in the literature or can be prepared by known methods The compounds of formula (I) may be prepared singly or as compound libraries comprising at least 2, e.g. 5 to 1000, preferably 10 to 100 compounds of formula (I). Compound libraries may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable derivatives thereof Pharmaceutically acceptable salts may be prepared conventionally by reaction with the appropriate acid or acid derivative.

The compounds of formula (I) and their pharmaceutically acceptable derivatives are useful for the treatment of diseases or disorders where an antagonist of a human orexin receptor is required such as obesity and diabetes; prolactinoma; hypoprolactinemia; hypothalamic disorders of growth hormone deficiency; idiopathic growth hormone deficiency; Cushing's syndrome/disease; hypothalamic-adrenal dysfunction; dwarfism; sleep disorders; sleep apnea; narcolepsy; insomnia; parasomnia; jet-lag syndrome; sleep disturbances associated with diseases such as neurological disorders, neuropathic pain and restless leg syndrome; heart and lung diseases; depression; anxiety; addictions; obsessive compulsive disorder, affective neurosis/disorder; depressive neurosis/disorder; anxiety neurosis; dysthymic disorder; behaviour disorder, mood disorder; sexual dysfunction; psychosexual dysfunction; sex disorder, sexual disorder, schizophrenia; manic depression; delerium; dementia; bulimia and hypopituitarism. The compounds of formula (I) or pharmaceutically acceptable derivatives thereof are also useful in the treatment of stroke, particularly ischaemic or haemorrhagic stroke. Furthermore the compounds of formula (I) or pharmaceutically acceptable derivatives thereof are also useful in blocking the emetic response.

The compounds of formula (I) and their pharmaceutically acceptable derivatives are particularly useful for the treatment of obesity, including obesity associated with Type 2 diabetes, sleep disorders, stroke and blocking the emetic response for example nausea and vomiting.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; post-operative pain; neuralgia; and tolerance to narcotics or withdrawal from narcotics.

The invention also provides a method of treating or preventing diseases or disorders where an antagonist of a human orexin receptor is required, which comprises administering to a subject in need thereof an effective amount of a compound of formula (I), or a pharmaceutically acceptable derivative thereof.

The invention also provides a compound of formula (I), or a pharmaceutically acceptable derivative thereof, for use in the treatment or prophylaxis of diseases or disorders where an antagonist of a human orexin receptor is required.

A further aspect of the invention is the use of N-[2-(7-chloro-quinolin-4-ylamino)ethyl]-N-methyl-phthalamic acid or N-methyl-n-[2-napthalen-2-ylaminoethyl]benzamide for use in the treatment of diseases or disorders where an antagonist of a human orexin receptor is required such as those described above.

The invention also provides the use of a compound of formula (I), or a pharmaceutically acceptable derivative thereof, in the manufacture of a medicament for the treatment or prophylaxis of diseases or disorders where an antagonist of a human orexin receptor is required.

The invention further provides for the use of of N-[2-(7-chloro-quinolin-4-ylamino)ethyl]-N-methyl-phthalamic acid or N-methyl-n-[2-napthalen-2-ylaminoethyl]benzamide, or a pharmaceutically acceptable derivative thereof, in the manufacture of a medicament for the treatment or prophylaxis of diseases or disorders where an antagonist of a human orexin receptor is required.

For use in therapy the compounds of the invention are usually administered as a pharmaceutical composition. The invention also provides a pharmaceutical composition comprising a compound of formula (I), or a pharmaceutically acceptable derivative thereof, and a pharmaceutically acceptable carrier.

The compounds of formula (I) and their pharmaceutically acceptable derivatives may be administered by any convenient method, e.g. by oral, parenteral, buccal, sublingual, nasal, rectal or transdermal administration, and the pharmaceutical compositions adapted accordingly.

The compounds of formula (I) and their pharmaceutically acceptable derivatives which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable derivative thereof, used in the treatment or prophylaxis of the abovementioned disorders or diseases will vary in the usual way with the particular disorder or disease being treated, the weight of the subject and other similar factors. However, as a general rule, suitable unit doses may be 0.05 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable derivatives the above figures are calculated as the parent compound of formula (I).

No toxicological effects are indicated/expected when a compound of formula (I) is administered in the above mentioned dosage range.

Human orexin-A has the amino acid sequence:

```
pyroGlu Pro Leu Pro Asp Cys Cys Arg Gln Lys Thr Cys Ser Cys Arg Leu
1               5                   10                  15
Tyr Glu Leu Leu His Gly Ala Gly Asn His Ala Ala Gly Ile Leu Thr
                20                  25                  30
Leu-NH2
```

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, *Drosophila* or *E. coli*. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into *Xenopus* oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The Descriptions D1–D11 illustrate the preparation of intermediates to compounds of the invention.

In the Examples $^1$H NMR's were measured at 250 MHz in CDCl$_3$ unless otherwise stated.

The following abbreviations are used herein;

HATU means O-(7-azabenzotriazol-1-yl)-N,N,N',N'-tetramethyluronium hexafluorophosphate DMF means N,N-dimethyl formamide Description 1: [2-(6,7-Difluoro-quinoxalin-2-ylamino)-ethyl]-methyl-carbamic acid dimethyl-ethyl ester A mixture of (2-amino-ethyl)-methyl-carbamic acid dimethyl-ethyl ester (1.01 g, 5.8 mmol), 2-chloro-6,7-difluoro-quinoxaline (1.00 g, 5.8 mmol) and N,N-diisopropylethylamine (3.02 ml, 17.4 mmol) in xylene (10 ml) was heated under argon at 80° C. for 18 h. The cooled reaction mixture was partitioned between ethyl acetate and water. The organic phase was washed with water, brine, dried (MgSO$_4$) and the solvent removed in vacuo. The residue was triturated with diethyl ether/pentane to afford the title compound as a pale orange solid.

Mass spectrum (API$^+$): Found 339 (MH$^+$). C$_{16}$H$_{20}$F$_2$N$_4$O$_2$ requires 338.

Description 2: N-(6,7-Difluoro-quinoxalin-2-yl)-N'-methyl-ethane-1,2-diamine. dihydrochloride An ice-cooled solution of [2-(6,7-difluoro-quinoxalin-2-ylamino)-ethyl]-methyl-carbamic acid dimethyl-ethyl ester, D1 (500 mg, 1.48 mmol) in methanol (20 ml) was treated with HCl in dioxane (4M solution, 4 ml). After stirring under argon at room temperature for 4 h the volatiles were removed in vacuo and the residue was triturated with diethyl ether to afford the title compound as a beige powder (100%).

¹H NMR δ: (D₆-DMSO) 2.51 (3H, s), 3.18 (2H, m), 3.69 (2H, m), 7.60 (1H, m), 7.87 (1H, m), 8.32 (1H, bs), 8.38 (1H, s), 8.98 (1H, bs).

Description 3: Methyl-[2-(2,2,2-trifluoro-ethanoylamino)-ethyl]-carbamic acid dimethyl-ethyl ester Trifluoroacetic anhydride (2.23 ml, 15.8 mmol) was added drop-wise to an ice-cooled stirring solution of (2-amino-ethyl)-methyl-carbamic acid dimethyl-ethyl ester (2.5 g, 14.4 mmol) and triethylamine (2.4 ml, 17.2 mmol) in dichloromethane (80 ml) under argon. After string for 1 h, the ice-bath was removed and stirring continued for a further 72 h. The reaction mixture was diluted with dichloromethane, washed with aqueous sodium bicarbonate solution, dried (MgSO₄) and the solvent removed in vacuo to afford the title compound as a colourless gum (3.61 g, 93%).

Mass spectrum (API⁻): Found 269 (M–H). $C_{10}H_{17}F_3N_2O_3$ requires 270.

Description 4: 5-(4-Fluoro-phenyl)-2-methyl-thiazole-4-carboxylic acid methyl-[2-(2,2,2-trifluoro-ethanoylamino)-ethyl]-amide An ice-cooled solution of methyl-[2-(2,2,2-trifluoro-ethanoylamino)-ethyl]-carbamic acid dimethyl-ethyl ester, D3 (3.61 g, 13.4 mmol) in dichloromethane (80 ml) was treated with trifluoroacetic acid (20 ml). After stirring at room temperature for 5 h the mixture was poured cautiously onto solid K₂CO₃ (excess)/ice. The product was extracted with dichloromethane (4×) then 10% methanol-dichloromethane (5×). The combined organics were dried (MgSO₄) and the solvent removed in vacuo. The resulting yellow gum (380 mg) was added to a stirring solution of 5-(4-fluoro-phenyl)-2-methyl-thiazole-4-carboxylic acid (530 mg, 2.2 mmol), N,N-diisopropylethylamine (1.17 ml, 6.7 mmol) and HATU (851 mg, 2.2 mmol). The reaction mixture was stirred at room temperature, under argon for 16 h, then partitioned between ethyl acetate and water. The organic phase was washed with water (2×), brine, dried (MgSO₄) and the solvent removed in vacuo. Chromatography (silica gel, 20–100% ethyl acetate-pentane) afforded the title compound as a colourless gum (443 mg).

Mass spectrum (API⁺): Found 390 (MH⁺). $C_{16}H_{15}F_4N_3O_2S$ requires 389.

Description 5: 5-(4-Fluoro-phenyl)-2-methyl-thiazole-4-carboxylic Acid (2-amino-ethyl)-methyl-amide A solution of 5-(4-fluoro-phenyl)-2-methyl-thiazole-4-carboxylic acid methyl-[2-(2,2,2-trifluoro-ethanoylamino)-ethyl]-amide, D4 (443 mg, 1.14 mmol) im methanol/water (30 ml/10 ml) was treated with solid K₂CO₃ (787 mg, 5.70 mmol) and stirred at room temperature, under argon for 16 h. The methanol was removed in vacuo. The residue was diluted with water and extracted with ethyl acetate (3×). The combined organics were dried (MgSO₄) and the solvent removed in vacuo to afford the title compound as a yellow gum (240 mg, 72%).

Mass spectrum (API⁺): Found 294 (MH⁺). $C_{14}H_{16}FN_3OS$ requires 293.

Description 6: (R,S)-(2-Amino-propyl)-carbamic acid tert-butyl ester

A solution of di-tert-butyl dicarbonate (13.9 g, 0.064 mol) in 1,4-dioxane (100 ml) was added dropwise to a stirring solution of (R,S)-propane-1,2diamine (37.4 g, 0.51 mol) in 1,4-dioxane (200 ml). After stirring at room temperature, under argon for 16 h the volatiles were removed in vacuo. The residue was dissolved in water and the resulting solution extracted with MDC (3×). The combined organics were dried (MgSO₄) and the solvent removed in vacuo to afford the title compound as a yellow oil (11.1 g, 100%).

Mass Spectrum (API⁺): Found 175 (MH⁺). $C_8H_{18}N_2O_2$ requires 174.

¹H NMR δ: 1.07 (3H, d, J=6 Hz), 1.29 (2H, bs), 1.44 (9H, s), 2.80–3.20 (3H, bm), 5.56 (1H, bt).

Description 7: (R,S)-[2-(3,4-dimethoxy-benzylamino)-propyl]-carbamic acid tert-butyl ester A stirring solution of (R,S)-(2-amino-propyl)-carbamic acid tert-butyl ester, D6 (3.28 g, 18.9 mmol) and 3,4-dimethoxy-benzaldehyde (3.15 g, 18.9 mmol) in 1,2-dichloro-ethane (75 ml) was treated with sodium triacetoxy-borohydride (6.02 g, 28.4 mmol) added portionwise. After stirring at room temperature, under argon for 16 h the reaction mixture was diluted with dichloromethane and washed with saturated K₂CO₃ solution. The organic phase was dried (MgSO₄) and the solvent removed in vacuo. Chromatography (silica gel, 0–100% pentane-ethyl acetate) afforded the title compound as an orange gum (4.12 g, 67%).

Mass Spectrum (API⁺): Found (MH⁺)323. $C_{17}H_{28}N_2O_4$ requires 324.

Description 8: (R,S)-[2-((3,4-Dimethoxy-benzyl)-{1-[5-(4-fluoro-phenyl)-2-methyl-thiazol-4-yl]-methanoyl}-amino)-propyl]-carbamic acid tert-butyl ester A solution of 5-(4-fluoro-phenyl)-2-methyl-thiazole-4-carboxylic acid (200 mg, 0.84 mmol) in DMF (20 ml) was treated sequentially with N,N-diisopropylethylamine (0.44 ml, excess), HATU (320 mg, 2.52 mmol) then after 15 min. (R,S)-[2-(3,4-dimethoxy-benzylamino)-propyl]-carbamic acid tert-butyl ester, D7 (272 mg, 0.84 mmol). The reaction mixture was stirred at room temperature, under argon for 16 h then partitioned between ethyl acetate and water. The organic phase was washed with water (3×), brine, dried (MgSO₄) and the solvent removed in vacuo to afford the title compound as a yellow gum (456 mg, 100%).

Mass Spectrum (API⁺): Found (MH⁺)544. $C_{28}H_{34}FN_3O_5S$ requires 543.

Description 9: (R,S)-5-(4-Fluoro-phenyl)-2-methyl-thiazole-4-carboxylic acid (2-amino-1-methyl-ethyl)-(3,4-dimethoxy-benzyl)amide An ice-cooled solution of (R,S)-[2-((3,4-dimethoxy-benzyl)-{1-[5-(4-fluoro-phenyl)-2-methyl-thiazol-4-yl]-methanoyl}-amino)-propyl]-carbamic acid tert-butyl ester, D8, (430 mg, 0.79 mmol) in dichloromethane (22.5 ml) was treated with trifluoroacetic acid (2.5 ml). After stirring at room temperature for 5 h the mixture was poured cautiously onto solid K₂CO₃ (excess)/ice. The product was extracted with dichloromethane (3×), the combined organics were dried (MgSO₄) and the solvent removed in vacuo to afford the title compound as a brown gum (100%).

Mass Spectrum (API⁺): Found (MH⁺)444. $C_{23}H_{26}FN_3O_3S$ requires 443.

Description 10: [2-(5-Bromo-pyrimidin-2-ylamino)-ethyl]-methyl-carbamic acid dimethyl-ethyl ester The title compound (2.40 g, 73%) was prepared from (2-amino-ethyl)-methyl-carbamic acid dimethyl-ethyl ester (1.74 g, 10 mmol), 2-chloro-5-bromo-pyrimidine (1.93 g, 10 mmol), N,N-diisopropylethylamine (3.87 g, 30 mmol) and K₂CO₃ (2.76 g, 20 mmol) according to the procedure described for Description 1.

Mass spectrum (API⁺): Found 230 (M-ᵗBOC). $C_{12}H_{19}{}^{79}BrN_4O_2$ requires 330.

Description 11: N-(5-bromo-pyrimidin-2-yl)-N'-methyl-ethane-1,2-diamine

An ice-cooled solution of [2-(5-bromo-pyrimidin-2-ylamino)-ethyl]-methyl-carbamic acid dimethyl-ethyl ester, D10 (2.32 g, 7.0 mol) in dichloromethane (90 ml) was treated with trifluoroacetic acid (10 ml). The reaction mixture was stirred for 2 h at room temperature, under argon then poured onto $K_2CO_3$ (excess)/ice. The aqueous layer was separated, washed with dichloromethane (3×) and the combined organics dried ($MgSO_4$) and the solvent removed in vacuo to afford the title compound (1.00 g, 61%).

Mass Spectrum (API$^+$): Found (MH$^+$)231. $C_7H_{11}^{79}BrN_4$ requires 230.

EXAMPLE 1

5-(4-Fluoro-phenyl)-2-methyl-thiazole-4-carboxylic acid [2-(6,7-difluoro-quinoxalin-2-ylamino)-ethyl]-methyl-amide A solution of 5-(4-fluoro-phenyl)-2-methyl-thiazole-4-carboxylic acid (50 mg, 0.21 mmol) in DMF (3 ml) was treated sequentially with N,N-diisopropylethylamine (0.20 ml, excess), HATU (79 mg, 0.21 mmol) then after 15 min. N-(6,7-difluoro-quinoxalin-2-yl)-N'-methyl-ethane-1,2-diamine.dihydrochloride, D2 (65 mg, 0.21 mmol). The reaction mixture was stirred at room temperature, under argon for 72 h then partitioned between diethyl ether and water. The organic phase was washed with water (3×), brine, dried ($MgSO_4$) and the solvent removed in vacuo. The residue was triturated with pentane to afford the title compound as a pale yellow powder (38 mg, 40%).

Mass spectrum (Electrospray LC/MS): Found (MH$^+$)458. $C_{22}H_{18}F_3N_5OS$ requires 457.

EXAMPLE 2

4-(4-Fluoro-phenyl)-1-methyl-1H-pyrazole-3-carboxylic acid [2-(6,7-difluoro-quinoxalin-2-ylamino)-ethyl]-methyl-amide The title compound was prepared from 4-4-fluoro-phenyl)-1-methyl-1H-pyrazole-3-carboxylic acid (46 mg, 0.21 mmol) and N-(6,7-difluoro-quinoxalin-2-yl)-N'-methyl-ethane-1,2-diamine.dihydrochloride, D2 (65 mg, 0.21 mmol) according to the procedure described for Example 1, as a yellow solid (65 mg, 71%).

Mass spectrum (Electrospray LC/MS): Found (MH$^+$) 441. $CH_{22}H_{19}F_3N_6O$ requires 440.

EXAMPLE 3

4-(4-Fluoro-phenyl)-1H-pyrazole-3-carboxylic acid [2-(6,7-difluoro-quinoxalin-2-ylamino)-ethyl]-methyl-amide The title compound was prepared from 4-(4-fluoro-phenyl)-1H-pyrazole-3-carboxylic acid (43 mg, 0.21 mmol) and N-(6,7-difluoro-quinoxalin-2-yl)-N'-methyl-ethane-1,2-diamine.dihydrochloride, D2 (65 mg, 0.21 mmol) according to the procedure described for Example 1, as a yellow solid (65 mg, 71%).

Mass spectrum (Electrospray LC/MS): Found (MH$^+$) 427. $C_{21}H_{17}F_3N_6O$ requires 426.

EXAMPLE 4

5-(4-Fluoro-phenyl)-2-methyl-thiazole-4-carboxylic acid [2-(benzooxazol-2-ylamino)-ethyl]-amide A solution of 5-(4-fluoro-phenyl)-2-methyl-thiazole-4-carboxylic acid (2-amino-ethyl)-methyl-amide, D5 (120 mg, 0.41 mmol) in THF (7 ml) was treated with triethylamine (0.057 ml) and 2-chlorobenzoxazole (0.047 ml, 0.41 mmol). The reaction mixture was stirred at room temperature, under argon for 16 h then the volatiles removed in vacuo. The residue was chromatographed (silica gel, 25% ethyl acetate-pentane) to afford the title compound as a white solid (97 mg, 58%).

Mass spectrum (Electrospray LC/MS): Found (MH$^+$) 411. $C_{21}H_{19}FN_4O_2S$ requires 410.

EXAMPLE 5

(R,S)-5-(4-Fluoro-phenyl)-2-methyl-thiazole-4-carboxylic acid [2-(benzooxazol-2-ylamino)-1-methyl-ethyl]-(3,4dimethoxy-benzyl)-amide The title compound was prepared from (R,S)-5-(4-fluoro-phenyl)-2-methyl-thiazole-4-carboxylic acid (2-amino-1-methyl-ethyl)-(3,4-dimethoxy-benzyl)-amide, D9 (380 mg, 0.86 mmol) and 2-chlorobenzoxazole (0.098 ml, 0.86 mmol), according to the procedure described for Example 4, as a white foam (150 mg, 31%).

Mass spectrum (Electrospray LC/MS): Found (MH$^+$) 561. $C_{30}H_{29}FN_4O_4S$ requires 560.

EXAMPLE 6

5-(4-Fluoro-phenyl)-2-methyl-thiazole-4-carboxylic acid [2-(5-bromo-pyrimidin-2-ylamino)-ethyl]-methyl-amide The title compound was prepared from 5-(4-fluoro-phenyl)-2-methyl-thiazole-4carboxylic acid (78 mg, 0.33 mmol) and N-(5-bromo-pyrimidin-2-yl)-N'-methyl-ethane-1,2-diamine, D11 (76 mg, 0.33 mmol), according to the procedure described for Example 1, as a solid (105 mg, 71%).

Mass spectrum (Electrospray LC/MS): Found (MH$^+$) 450. $C_{18}H_{17}^{79}BrFN_5OS$ requires 449.

It is to be understood that the present invention covers all combinations of particular and preferred subgroups described herein above.

Determination of Orexin-1 Receptor Antagonist Activity

The orexin-1 receptor antagonist activity of the compounds of formula (I) was determined in accordance with the following experimental method.

Experimental Method

HEK293 cells expressing the human orexin-1 receptor were grown in cell medium (M medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 µl/well into 96-well black clear bottom sterile plates from Costar which had been pre-coated with 10 µg/well of poly-L-lysine from SIGMA. The seeded plates were incubated overnight at 37° C. in 5% $CO_2$.

Agonists were prepared as 1 mM stocks in water:DMSO (1:1). $EC_{50}$ values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 3.0 nM human orexin-A using 11× half log unit dilutions in Tyrode's buffer containing 10% DMSO and probenecid.

On the day of assay 50 µl of cell medium containing probenecid (Sigma) and Fluo3AM (Texas Fluorescence Laboratories) was added (Quadra, Tomtec) to each well to give final concentrations of 2.5 mM and 4 µM, respectively. The 96-well plates were incubated for 90 min at 37° C. in 5% $CO_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument and maintained at 37° C. in humidified air. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jerman, TiPS, 1995, 16, 413–417) to generate a concentration effect value. Antagonist Kb values were calculated using the equation:

$$K_b = IC_{50}/(1+([3/EC_{50}])$$

where $EC_{50}$ was the potency of human orexin-A determined in the assay (in nM terms) and $IC_{50}$ is expressed in molar terms.

Compounds of Examples tested according to this method had pKb values 6.4 to 7.4 at the human cloned orexin-1 receptor.

The orexin-2 receptor antagonist activity of the compounds of formula (I) was determined in accordance with the following experimental method.

Experimental Method

CHO-DG44 cells expressing the human orexin-2 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37C in 5% $CO_2$.

Agonists were prepared as 1 mM stocks in water:DMSO (1:1). $EC_{50}$ values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 10.0 nM human orexin-A using 11× half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96well plates were incubated for 60 min at 37C in 5% $CO_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37C in 5% $CO_2$ for 30 min. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jerman, TiPS, 1995, 16, 413–417) to generate a concentration effect value. Antagonist Kb values were calculated using the equation:

$$Kb = IC50/(1+([3/EC50])$$

where EC50 was the potency of human orexin-A determined in the assay (in nM terms) and IC50 is expressed in molar terms.

Compounds of Examples tested according to this method had pKb values in the range <6.6 to 7.4 at the human cloned orexin-2 receptor.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims:

The invention claimed is:

1. A compound of formula (I):

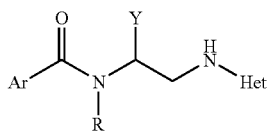

(I)

wherein:

R represents an optionally substituted $(C_{1-4})$alkyl group;

Y represents hydrogen or an optionally substituted $(C_{1-4})$ alkyl group;

Het represents an optionally substituted 5- or 6-membered heteroaryl group containing up to 3 heteroatoms selected from N, O, and S, or an optionally substituted bicyclic heteroaryl group containing up to 3 heteroatoms selected from N, O and S;

Ar represents a phenyl, thienyl, pyrrolyl, oxazolyl, thiazolyl, oxadiazolyl, thiadiazolyl, pyridyl, triazolyl, triazinyl, pyridazinyl, pyrimidinyl, isothiazolyl, isoxazolyl, pyrazinyl pyrazolyl, naphthyl, quinolinyl, napththyridinyl, benzimidazolyl, benzoxazolyl, isoquinolinyl, quinoxalinyl or quinazolinyl group, wherein said group is optionally substituted and is substituted by $R^3$;

$R^3$ independently represents hydrogen, an optionally substituted $(C_{1-4})$alkoxy group, halo, an optionally substituted $(C_{1-6})$alkyl group, an optionally substituted phenyl group, or an optionally substituted 5- or 6-membered heterocyclic ring group containing up to 3 heteroatoms selected from N, O and S;

wherein the substituents for the optionally substituted R, Y, Het, Ar, and $R^3$ groups are selected from halogen, hydroxy, oxo, cyano, nitro, $(C_{1-4})$alkyl, $(C_{1-4})$alkoxy, halo$(C_{1-4})$alkyl, halo$(C_{1-4})$alkoxy, $(C_{1-4})$acyl, aryl, aryl $(C_{1-4})$alkyl, aryl$(C_{1-4})$alkoxy, $(C_{1-4})$alkylthio, $(C_{1-4})$ alkylamino$(C_{1-4})$alkyl, hydroxy$(C_{1-4})$alkyl, hydroxy $(C_{1-4})$alkoxy, $(C_{1-4})$alkoxy$(C_{1-4})$alkyl, $(C_{3-6})$cycloalkyl $(C_{1-4})$alkoxy, $(C_{1-4})$alkanoyl, $(C_{1-4})$alkoxycarbonyl, $(C_{1-4})$alkylsulfonyl, $(C_{1-4})$alkylsulfonyloxy, $(C_{1-4})$ alkylsulfonyl$(C_{1-4})$alkyl, arylsulfonyl, arylsulfonyloxy, arylsulfonyl$(C_{1-4})$alkyl, $(C_{1-4})$alkylsulfonamido, $(C_{1-4})$ alkylamido, $(C_{1-4})$alkylsulfonamido$(C_{1-4})$alkyl, $(C_{1-4})$ alkylamido$(C_{1-4})$alkyl, arylsulfonamido, arylcarboxamido, arylsulfonamido$(C_{1-4})$alkyl, arylcarboxamido $(C_{1-4})$alkyl, aroyl, aroyl$(C_{1-4})$alkyl, aryl$(C_{1-4})$alkanoyl, $R^aR^bN$—, $R^aR^bN(CH_2)n$-, $R^aR^bN(CH_2)nO$—, $R^aOCO$ $(CH_2)_r$, $R^aCON(R^b)(CH_2)_r$, $R^aR^bNCO(CH_2)_r$, and $R^aR^bNSO_2(CH_2)_r$.

wherein each of $R^a$ and $R^b$ independently represents a hydrogen atom or a $(C_{1-4})$alkyl group or where appropriate $R^aR^b$ forms part of a $(C_{3-6})$azacycloalkane or a $(C_{3-6})$(2-oxo)azacycloalkane ring, n represents an integer from 1 to 4, and r represents zero or an integer from 1 to 4, or wherein when the substituent is $R^aR^bN(CH_2)n$- or $R^aR^bN(CH_2)nO$, $R^a$ with at least one $CH_2$ of the $(CH_2)n$ portion of the group form a $(C_{3-6})$azacycloalkane and $R^b$ represents hydrogen a $(C_{1-4})$alkyl group or with the nitrogen to which it is attached forms a second $(C_{3-6})$ azacycloalkane;

and wherein, in groups Ar and Het, substituents positioned ortho to each other are optionally linked to from a fused ring, or a pharmaceutically acceptable salt thereof, provided the compound is not N-[2-(7-chloro-quinolin-4-ylamino)ethyl]-N-methyl-phthalamic acid; or N-methyl-n-[2-napthalen-2-ylaminoethyl]benzamide.

2. A compound according to claim 1 wherein Het represents an optionally substituted pyrimidinyl, benzoxazolyl or quinoxalinyl group.

3. A compound according to claim 1 wherein Ar represents an optionally substituted thiazolyl or pyrazolyl group.

4. A compound according to claim 1 wherein $R^3$ represents an optionally substituted phenyl group.

5. A compound: 5-(4-Fluoro-phenyl)-2-methyl-thiazole-4-carboxylic acid [2-(6,7-difluoro-quinoxalin-2-ylamino)-ethyl]-methyl-amide; 4-(4-Fluoro-phenyl)-1-methyl-1H-pyrazole-3-carboxylic acid [2-(6,7-difluoro-quinoxalin-2-ylamino)-ethyl]-methyl-amide; 4-(4-Fluoro-phenyl)-1H-pyrazole-3-carboxylic acid [2-(6.7-difluoro-quinoxalin-2-ylamino)-ethyl]-methyl-amide; 5-(4-Fluoro-phenyl)-2-methyl-thiazole-4-carboxylic acid [2-(benzooxazol-2-ylamino)-ethyl]-amide; (R,S)-5-(4-Fluoro-phenyl)-2-methyl-thiazole-4-carboxylic acid [2-(benzooxazol-2-ylamino)-1-methyl-ethyl]-(3,4-dimethoxy-benzyl)-amide; 5-(4-Fluoro-phenyl)-2-methyl-thiazole-4-carboxylic acid [2-(5-bromo-pyrimidin-2-ylamino)-ethyl]-methyl-amide; or a pharmaceutically acceptable salt of any one thereof.

6. A pharmaceutical composition comprising the compound of formula (I) as defined in claim 1, or a pharmaceutically acceptable salt thereof, and a pharmaceutically acceptable carrier.

7. A method of treating a disease or disorder where an antagonist of a human orexin receptor is required, wherein said disease or disorder is selected from obesity and obesity associated with Type 2 diabetes, which comprises administering to a subject in need thereof an effective amount of the compound of formula (I) as defined in claim 1, or a pharmaceutically acceptable salt thereof.

8. A method of treating insomnia which comprises administering to a subject in need thereof an effective amount of the compound of formula (I) as defined in claim 1, or a pharmaceutically acceptable salt thereof.

9. A compound according to claim 2 wherein the optionally substituted pyrimidinyl, benzoxazolyl or quinoxalinyl group is optionally substituted by halogen, cyano, $(C_{1-4}$alkyl, hydroxy$(C_{1-4}$alkyl, $(C_{1-4}$acyl, $(C_{1-4}$alkoxy$(C_{1-4}$alkyl, $R^aR^bNCO(CH_2)$, $R^aR^bN(CH_2)n$ or $R^aR^bN$.

10. A compound according to claim 2 wherein the optionally substituted pyrimidinyl, benzoxazolyl or quinoxalinyl group is optionally substituted by is optionally substituted by a phenyl ring optionally substituted by a halogen, cyano, $(C_{1-4})$alkanoyl or $(C_{1-4})$alkylsulfonyl group.

11. A compound according to claim 2 wherein the optionally substituted pyrimidinyl, benzoxazolyl or quinoxalinyl group is optionally substituted by a 5- or 6-membered heterocyclic ring optionally substituted by a $(C_{1-2})$alkyl or $R^aR^bN$— group.

12. A compound according to claim 3 wherein the optionally substituted thiazolyl or pyrazolyl group is optionally substituted by halogen, cyano, $(C_{1-4})$alkyl, hydroxy$(C_{1-4})$ alkyl, $R^aR^bN(CH_2)n$ or $R^aR^bN$.

13. A compound according to claim 4 wherein $R^3$ represents a phenyl optionally substituted by a group selected from halogen, $R^aR^bN$ and $R^aR^bN(CH_2)nO$.

14. A compound according to claim 1 wherein:

R represents methyl;

Y represents hydrogen or a $(C_{1-4})$alkyl group;

Het represents a pyrimidinyl, benzoxazolyl or quinoxalinyl group, which is:

optionally substituted by halogen, cyano, $(C_{1-4})$alkyl, hydroxy$(C_{1-4})$alkyl, $(C_{1-4})$acyl, $(C_{1-4})$alkoxy,$(C_{1-4})$ alkyl, $R^aR^bNCO(CH_2)$, $R^aR^bN(CH_2)n$, or $R^a R^bN$, or optionally substituted by a phenyl ring optionally substituted by a halogen, cyano, $(C_{1-4})$alkanoyl or $(C_{1-4})$alkylsulfanoyl group, or optionally substituted by a 5- or 6-membered heterocyclic ring optionally substituted by a $(C_{1-2})$alkyl or $R^aR^bN$— group;

Ar represents thiazolyl or pyrazolyl, optionally substituted by halogen, cyano, $C_{1-4}$alkyl, hydroxy$(C_{1-4})$alkyl, $R^aR^bN(CH_2)n$ or $R^aR^bN$; and $R^3$ represents a phenyl optionally substituted by a group selected from a halogen, $R^a R^bN$ and $R^aR^bN(CH_2)nO$.

15. A method of treating a disease or disorder where an antagonist of a human orexin receptor is required, wherein said disease or disorder is selected from jet-lag syndrome and disturbed circadian rhythms, which comprises administering to a subject in need thereof an effective amount of the compound of formula (I), or the pharmaceutically acceptable salt thereof, as defined in claim 1.

* * * * *